United States Patent [19]

Nakamura

[11] Patent Number: 5,520,057
[45] Date of Patent: May 28, 1996

[54] TEST BILLET FOR USE IN PRESS LOAD TEST AND LOAD TEST METHOD THEREOF

[75] Inventor: Masatoshi Nakamura, Osaka, Japan

[73] Assignee: Kurimoto, Ltd., Osaka, Japan

[21] Appl. No.: 531,886

[22] Filed: Sep. 22, 1995

Related U.S. Application Data

[63] Continuation of Ser. No. 199,937, Feb. 22, 1994, abandoned.

[51] Int. Cl.$^6$ .............................. G01N 3/00; G01N 11/00
[52] U.S. Cl. ........................ 73/823; 73/785; 73/862.621
[58] Field of Search .............................. 73/785, 823, 826, 73/866.4, 862.381, 862.542, 862.621

[56] References Cited

U.S. PATENT DOCUMENTS

| | | | |
|---|---|---|---|
| 2,482,147 | 9/1949 | Bashore | 73/823 |
| 2,637,203 | 5/1953 | Gehman | 73/823 |
| 2,667,699 | 2/1954 | Buist et al. | 73/826 |
| 2,917,920 | 12/1959 | Robinette, Jr. et al. | 73/826 |
| 3,382,709 | 5/1968 | Sorensen | 73/826 |

FOREIGN PATENT DOCUMENTS

| | | | |
|---|---|---|---|
| 0418490 | 3/1991 | European Pat. Off. | 73/862.621 |
| 60-235037 | 11/1985 | Japan | 73/826 |
| 0905663 | 2/1982 | U.S.S.R. | 73/862.621 |
| 1753345 | 8/1992 | U.S.S.R. | 73/826 |
| 0480060 | 2/1938 | United Kingdom | 73/826 |
| 1026556 | 4/1966 | United Kingdom | 73/862.621 |

OTHER PUBLICATIONS

G. Greetham, "Production and tensile testing of strain-free metal specimens", Journal of Scientific Instruments, vol. 37, May 1990, pp. 160–162.

*Primary Examiner*—Richard Chilcot
*Assistant Examiner*—George M. Dombroske
*Attorney, Agent, or Firm*—Jones, Tullar & Cooper

[57] ABSTRACT

The present invention has an object of simply and accurately measuring a load applied to a mechanical press. A test billet obtained from material of which the mechanical strength is uniform and which is finished precisely is placed on the press and pressed between a slide and a bed of a press, whereby an upsetting amount and a pressure at that time of pressing the billet are measured by a load cell. As a result, a press load, which may be calculated by establishing as functions such elements as material, deformation amount, and working speed of a test billet, can be accurately obtained by a simple measurement of the test billet to which established properties have preliminarily been given.

5 Claims, 4 Drawing Sheets

FIG. I(A)
FIG. I(B)
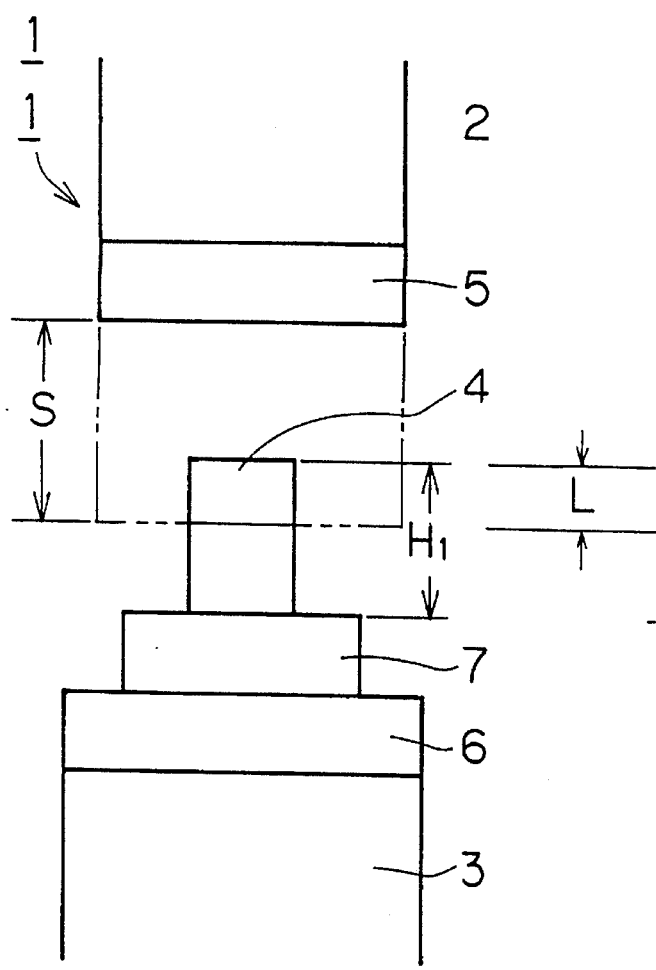
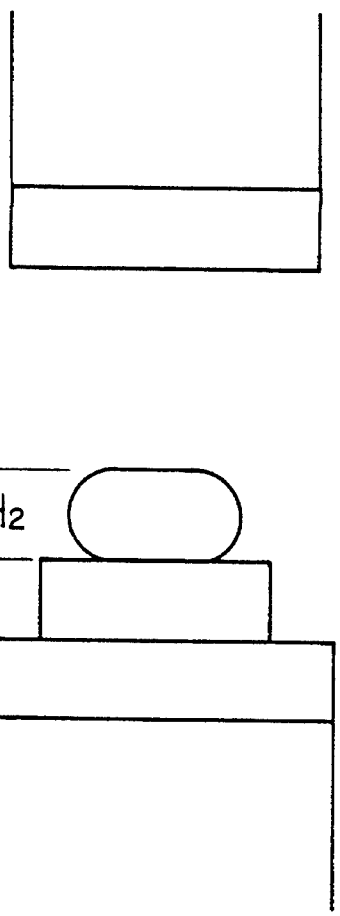

TEST BILLET FOR USE IN PRESS LOAD TEST AND LOAD TEST METHOD THEREOF

This is a continuation of application Ser. No. 08/199,937 filed on Feb. 22, 1994 now abandoned

BACKGROUND OF THE INVENTION

1. Field of the Invention

The present invention relates to a load test for a press and, more particularly, to a technique for detecting the actual state of a mechanical press.

2. Prior Arts

In hydraulic presses, there is almost no problem in measuring load since a load applied during operation of the press can be directly and visually detected by an oil pressure gauge, because the speed at which load is applied is not high. On the other hand, in mechanical presses, visual detection of the dynamic load is not easy as compared with hydraulic presses, because the load is applied with a strong impact. Besides, there are further essential problems incident to presses of this type.

With regard to a conventional measuring device mounted on a mechanical press, it has been heretofore known to employ means in which a load cell (strain gauge or dial gauge) is secured to a frame or post of the press, and by which, in a load test, a strain produced in the mechanical structure, such as the frame of the press, is measured, or variations in pressure produced in the incorporated hydraulic system are detected and electrically converted, thereby finally detecting the applied load. With such conventional means, however, a serious problem arises and must be solved with a view toward an accurate measurement of the load. This is so because dynamic load is usually applied with a strong impact. Moreover, the shape of a pressed product to be transferred to a die is not always lengthwise and breadthwise symmetrical, but is at times unevenly one-sided in most presses and, therefore, it may be said that, in most cases, a load is not applied uniformly but applied rather eccentrically in the form of a so-called eccentric load.

Further, in forging presses, multistage production dies are popularly employed, in which molds for two or more stages are arranged in one die and a material to be forged is timely transferred with the advance of the forging process. In such a multistage production forging die, the mentioned eccentric load takes place in all of the forging stages except the center part. Without accurately detecting such eccentric loading to adjust the bottom dead point appropriately, there is a possibility that an unexpected overload will be partially applied, eventually resulting in strain and/or cracking of the equipment and/or material. In spite of such a possible danger of breakdown, accurate measurement of the eccentric load is very difficult, which is another problem to be solved. Several attempts have been proposed to solve the mentioned problems.

For example, in the Japanese Laid-Open Patent Publication (unexamined) No. 54-42081, as illustrated in FIG. 3, a load measuring unit 102, on which a load cell 101 is placed and which is provided with a strain enhancement function, is prepared; then two posts located at positions of point symmetry with respect to the center point of the cross-section of a mechanical press are selected; two positions of point symmetry with respect to the center point of the cross-section of each post are further selected; a load unit like that mentioned above, is then mounted at each of the selected positions; and the output from each unit is transmitted to a dynamic strain type of load meter to measure a forging load. Publication No. 54-42081 discloses that, as a result of employing the mentioned arrangement, the conventional problem of inaccurate load measurement, which may lead to erroneous adjustment of the bottom dead point and sometimes result in press mechanism breakdown, can be successfully prevented, and load measurement has been improved to the extent of enabling detection of an accurate value of an eccentric load.

In the case of a mechanical press, however, a load is applied with strong impact in a moment, and therefore it is essential as a fatally important requirement to measure such a momentary load accurately and adjust the bottom dead point appropriately.

It is to be noted that the load measuring device is secured to any part of the press body, and accordingly, not only the press body but also the load measuring device itself will receive a strong shock and a high temperature, both incidental and peculiar to mechanical presses. This means that the load measuring device, being a delicate precision instrument, is exposed to the hardest condition as compared with other precision instruments and, therefore, there still remains a further problem that the reliability of a value measured by the load measuring device is lost in a rather short time with the operation of the press. The prior art mentioned with reference to FIG. 3 is not free from this problem, either.

To meet this problem, and overcome such a possibility of losing reliability, maintenance work is an essential requirement because working a press safely cannot go on without securing at all times the reliability of the mounted measuring device itself. Thus, in a working spot of the forging, where quality control is advanced, accurate load detection must be carried out repeatedly by inserting a separate hydraulic press into a portion of a mechanical press where load is applied.

FIG. 4 illustrates a press body associated with a conventional method for detecting a measured load. In this press body, a test hydraulic cylinder 103 is inserted between a slide 2 and a bed 3 of a mechanical press body 1, and the hydraulic cylinder 103 is provided with a sensor 104, a hydraulic device 105 and a measuring device 106, thereby forming a measuring circuit. With such an arrangement, the mechanical press 1 is put into operation, then a load thereof is transmitted to the hydraulic cylinder, and a value obtained which is converted and outputted to the measuring device.

In a test of this kind, not only expert techniques but also special equipment are required. Normally, it is nearly impossible to have such equipment in an average press working plant. In actuality, therefore, service engineers are sent by the manufacturer of the mechanical press, when requested by the user, to provide the mentioned kind of test service. Accordingly, there arise unavoidable problems such as the cost of the test service, loss caused by the suspension of routine operation to carry out such a test, shortage of skilled measuring service engineers, etc., eventually resulting in difficulty of carrying out sufficient maintenance of the press. Further, in the case of a forging press of large load, a test hydraulic cylinder of large capacity is required, and other auxiliary instruments must also be large corresponding to such a large capacity. On the part of the manufacturer, it may be a heavy burden to assort various kinds of test hydraulic cylinders and take them to the user's facility. Furthermore, in the case of forging presses, it is an essential requirement to measure and obtain the mentioned eccentric load, particularly in a multistage die. However, in carrying out such a measurement, there is actually no room for installing the axis of the test hydraulic cylinder of large capacity just on the eccentric position of the measurement, thus there is a spacial restriction in the measurement of the eccentric load, which is a further problem to be solved.

SUMMARY OF THE INVENTION

The present invention was made to solve the above-discussed problem and has as an object of the invention to provide a method for simply measuring the actual maximum load of the mechanical press, irrespective of the shape thereof.

To accomplish the foregoing object, there is provided, according to the present invention, a test billet for use in a press load test, the mechanical strength of which is adjusted to be uniform and which is formed to be uniformly cylindrical, characterized in that a preliminarily, established specific correlation between the press load and the plastic deformation amount is given to the billet.

There is also provided according to the method aspect of the present invention a method for using a test billet comprising the steps of: placing the test billet at a required position coincident with the press load point of the press, in such a manner so as to be interposed and pressed therein; measuring the amount of plastic deformation of the test billet; and calculating an actual press load at the load point from a known specific relational expression.

In calculating a load needed for press working, it is important to know what type of deformation resistance curve a material to be pressed has. In this regard, utilization of the deformation resistance curve obtained by testing the material used in the analysis is not always desirable, because the problem to be solved may be more complicated and sometimes the analysis itself becomes impossible. Therefore, for practical analysis purposes, the deformation resistance curve is generally simplified for the required calculations. There are various factors which complicate the deformation resistance, principal among which factors are strain influence, temperature influence, rate of strain influence, etc. Strain influence is exerted on work hardening and can be generally expressed as $\delta = \alpha \beta^n$: where n indicates a work hardening index also referred to as an n-value which is an element produced by lattice structure strain which takes place at the time of press working as a result of plastic deformation of the metallic material; and a indicates a coefficient proper to metallic material, which is determined depending upon the microscopic or macroscopic structure, particularly the crystal grain size or the flow of structure which are presented differently depending upon components and the heat history of the material. This $\alpha$-value is a constant and can be reliably adopted as a measurement reference for materials obtained from the same steel lot under sufficient quality control, and formed by precision finishing to have the same dimensions.

The mentioned rate of strain influence is also one of the principal factors, and within a certain range of rate of strain, deformation resistance 6 under a certain strain $\gamma$ can be generally expressed as $\delta = K\gamma^m$: where K indicates a deformation resistance at a unit rate of strain, and m indicates a dependency index of rate of strain.

For actually calculating a load, it is effective to associate these factors as reasonably as possible to obtain a relational expression approximate to the actual load. And for this purpose, the following expression is generally adopted:

$$\delta = \alpha\beta^n\gamma^m \tag{1}$$

where

δ: deformation resistance of a metal
α: proper value relative to the material considered
β: strain amount
γ: rate of strain
n: work hardening index (index relative to the degree of work)
m: dependency index of the rate of strain (index relative to the rate of work).

The expression (1) is a general expression for the plastic deformation of a metallic material for the load test of a press. The expression (1) is for the condition shown in FIG. 1(A), while for the factors obtained at the time of the deforming operation of the press shown in FIG. 1(B), the following comparison can be made:

δ: press load: T
α: element relative to material of test billet: M
$\beta^n$: element relative to upsetting amount: L
$\gamma^m$: element relative to slide speed (rotation speed of eccentric shaft): V It is understood from the above that the press load T is decided depending upon the element M relative to the material of the test billet, the element L relative to the deformation amount, and the element V relative to the rate of working, thus the following expression is obtained:

$$T = f(M \cdot L \cdot V) \tag{2}$$

Among the above elements, the element relative to the slide speed is a proper known value determined depending upon the specification of the press. The element relative to the material can be assured to be a reliable constant value at all times depending upon the preparation method of the test billet. In the preparation of the test billet, it is an essential requirement to be established that the internal structure of the test billet is adjusted to be uniform by a complete heat treatment, and the surface roughness thereof is formed to conform to a certain standard by machining, so that the same plastic deformation occurs, without fail, and is repeated with respect to the same load. On the condition that these elements are constant, the function of the expression (2) is variable and simply depends upon the element L relative to the deformation amount and, as a result, the press load can be calculated instantly just by measuring the upsetting amount.

As described above, in the present invention, the actual load of a mechanical press, the measurement of which is difficult due to the quick and strong movement of the press and which may often cause a measurement device to get out of order, can be now detected almost exactly by a quite simple method, and that it is no longer necessary to use precision measurement equipment of a large size at all, as has been required in the prior art. The technical advantage of the present invention is very large particularly in the measurement of eccentric loads under difficult measuring conditions. Accordingly, not only are the problems of cost incurred in ordering the load test, shortage of skilled measuring engineers, etc. done away with, but also uneconomical suspension of operation of the press for the troublesome workings of mounting the measuring instruments, carrying out the test, and dismounting the instrument are no longer necessary, resulting in productivity improvement. Since a load can be easily measured, as mentioned above, there arise further advantages such that inspection on whether or not the mounted load measuring device is operating without error can be easily carried out, and that even in the case of an unavoidable eccentric load depending upon the shape of die, any press load can be measured easily each required time by making an appropriate adjustment (by shifting the bottom death point), whereby damage to the press can be prevented due to unexpected eccentric loads.

Other objects, features and advantages of the present invention will become apparent in the course of the following description with reference to the accompanying drawings.

BRIEF DESCRIPTION OF THE DRAWINGS

FIG. 1(A) and FIG. 1(B) are respectively front views showing the basic principle of the present invention;

DESCRIPTION OF THE PREFERRED EMBODIMENT

FIG. 1(A) and FIG. 1(B) are respectively schematic views for explaining a function of the present invention. Referring to FIG. 1(A), a cylindrical test billet 4 is vertically placed between a slide 2 and a bed 3 of a mechanical press 1 in which a large technical advantage of the present invention is particularly expected. When actuating the press, the slide 2 comes down and executes a stroke S and presses the test billet 4 of axial length $H_1$, whereby a plastic deformation takes place. As a result, the axial length $H_1$ is changed to a length $H_2$, thus the upsetting amount of this press is $H_1-H_2=L$. A load T of the press is obtained by measuring a deformation resistance value of the test billet under operation with a load cell.

Figure 2:
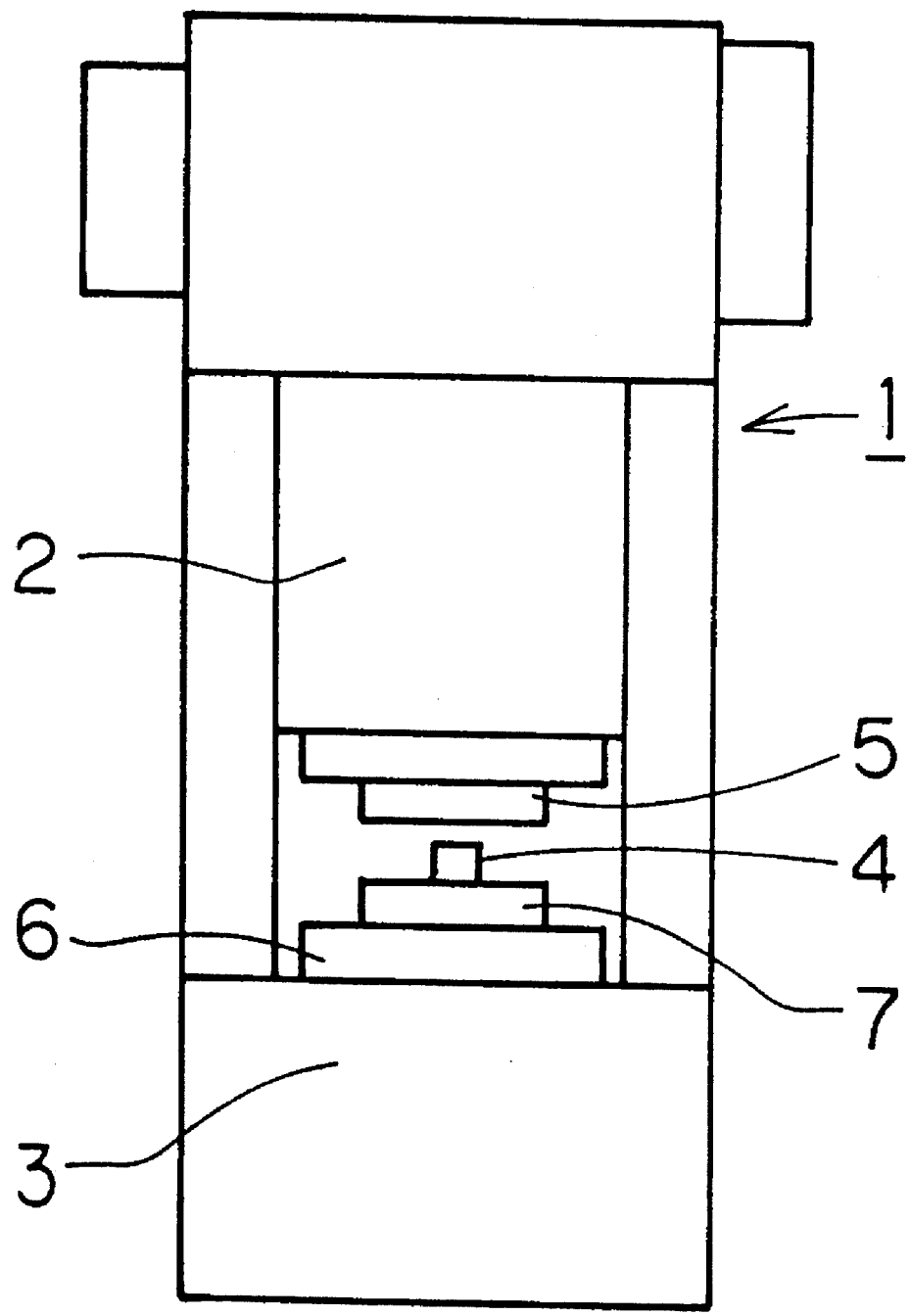
FIG. 2 is a front view showing an embodiment according to the present invention.
Figure 3:
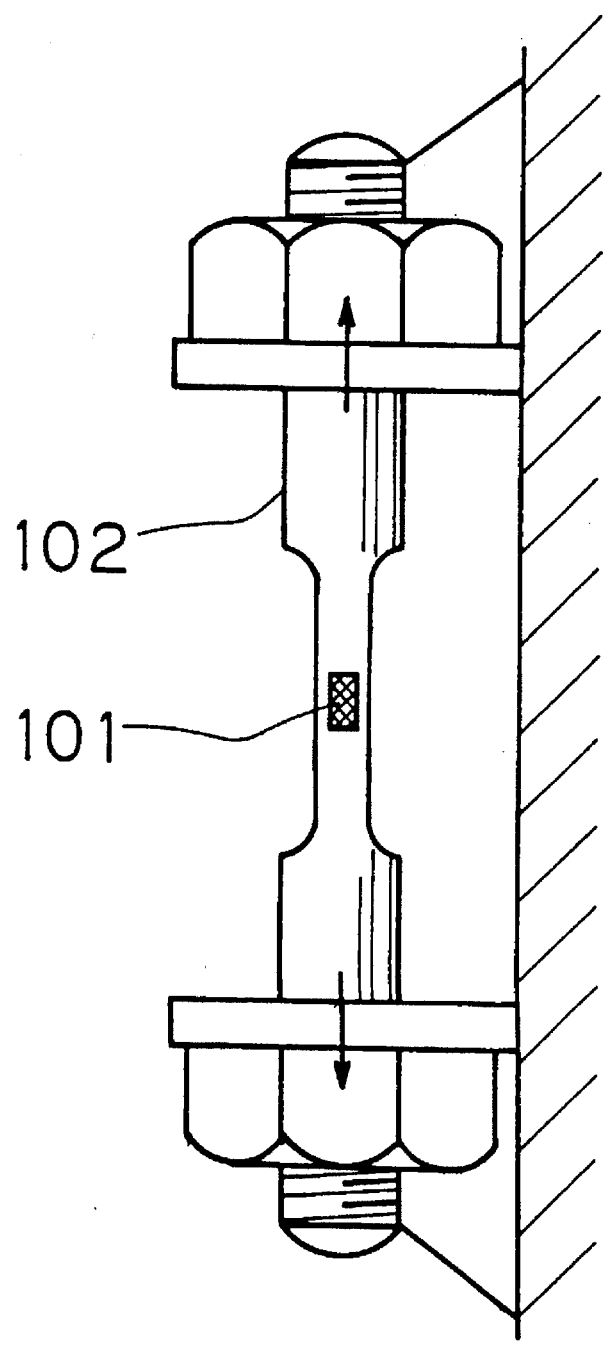
FIG. 3 is a front view showing prior art.
Figure 4:
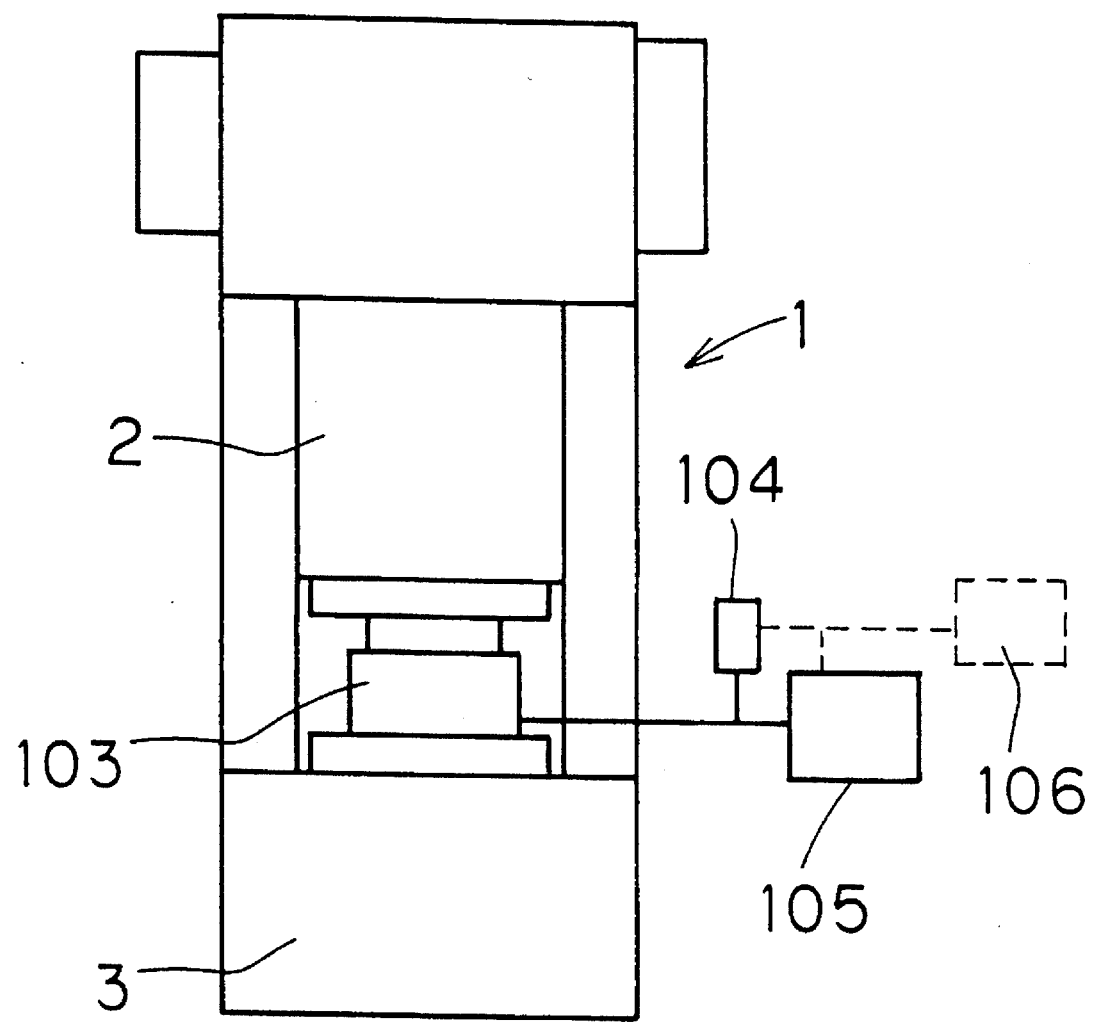
FIG. 4 is a front view showing another prior art.

Described hereinafter is an embodiment of the present invention. A test billet was picked up from a mass-produced product, the material of which was selected from the components set forth in JIS S30C. The billet was obtained by machining from a steel of which the specific mechanical strength is assured by the prescribed hardening and tempering process and the finish is assured to have a surface roughness conforming to the precision finish according to JIS. This test billet was accompanied by a diagram (or expressions) showing a preliminarily detected particular relation between load and deformation. This test billet was cylindrical being 110 mm in diameter and 30 mm in height. In the measurement, as illustrated in FIGS. 1(A), 1(B) and FIG. 2, an upper pressure disk 5 was mounted on the slide 2 of the mechanical press 1, and a lower pressure disk 6 was mounted on the bed 3. A load cell 7 was placed on the lower pressure disk and the test billet 4 was further placed vertically on the load cell, then the press was started. In the case where measurement of an eccentric load is required, it is a matter of course that the test billet should be placed so that the axis of the test billet coincides with the load point where a concentrated load is applied. The element relative to the deformation amount is an upsetting amount L, and the revolution speed (rpm) of the press was employed as the element relative to the deformation speed.

A following Table 1 shows data obtained by the test which relates the press load T, press revolution V, and upsetting amount L.

TABLE 1

| Upsetting amount L (mm) | Press Revolution V (rpm) | Press Load T (ton) |
| --- | --- | --- |
| 1.5 | 45 | 736 |

TABLE 1-continued

| Upsetting amount L (mm) | Press Revolution V (rpm) | Press Load T (ton) |
| --- | --- | --- |
| 1.5 | 60 | 736 |
| 1.5 | 75 | 760 |
| 5.5 | 45 | 1184 |
| 5.5 | 60 | 1172 |
| 5.5 | 75 | 1188 |
| 9.7 | 45 | 1580 |
| 9.7 | 60 | 1630 |
| 9.7 | 75 | 1600 |

It was acknowledged from the above table that there was a clear and significant correlation between the press load T and the upsetting amount L of the test billet, but that there was no clear correlation between the press load T and the press revolution V under a constant upsetting amount L. It was acknowledged by the test that the value of the press load T was within the error range of 3% even when the press revolution was ignored as far as presses of the same type were employed. As a result, it may be said that the press load T can be simply calculated just by starting a press and measuring a length of the upsetting amount $L(=H_1-H_2)$ on the condition that a test billet of established properties is employed.

I claim:

1. A metallic test billet used for load testing a mechanical press producing an impact load, said metallic test billet being uniformly cylindrical and characterized in that the amount of plastic deformation of said metallic test billet in the form of a difference in length of said metallic test billet before and after loading, said length being measured in the direction of loading, is correlated to a specific load of the mechanical press.

2. The metallic test billet as defined in claim 1, wherein said metallic test billet is steel.

3. The metallic test billet as defined in claim 1, wherein the metallic material is responsive to the following relationship:

$$\delta = \alpha \beta^n \gamma^m$$

where:

$\delta$: is the deformation resistance of the metal $\alpha$: is a coefficient value of the metal $\beta$: is the strain amount $\gamma$: is the rate of strain n: is the work hardening index m: is the dependency index of the rate of strain.

4. A method of testing the load of a mechanical press producing an impact load using a metallic test billet, comprising the steps of:

establishing a relationship between the plastic deformation of the metallic test billet and a specific load of the mechanical press;

placing the metallic test billet on the mechanical press at a press load point position where the press load is applied;

applying a press load to the test billet;

measuring the plastic deformation of the metallic test billet under load in the form of a difference in length of said metallic test billet before and after loading, said length being measured in the direction of loading; and calculating an actual press load at the press load point position from said plastic deformation and said relationship.

5. The method as defined in claim 4, wherein the relationship is:

$$\delta = \alpha \beta^n \gamma^m$$

where:
- $\delta$: is the deformation resistance of the metal
- $\alpha$: is a coefficient value of the metal
- $\beta$: is the strain amount
- $\gamma$: is the rate of strain
- n: is the work hardening index
- m: is the dependency index of the rate of strain.

* * * * *